United States Patent
Wagner et al.

(10) Patent No.: US 7,117,035 B2
(45) Date of Patent: Oct. 3, 2006

(54) SUBCUTANEOUS CARDIAC STIMULATION SYSTEM WITH PATIENT ACTIVITY SENSING

(75) Inventors: Darrell Orvin Wagner, Isanti, MN (US); Paul Haefner, Circle Pines, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 351 days.

(21) Appl. No.: 10/816,464

(22) Filed: Apr. 1, 2004

(65) Prior Publication Data

US 2004/0220633 A1 Nov. 4, 2004

Related U.S. Application Data

(60) Provisional application No. 60/462,272, filed on Apr. 11, 2003.

(51) Int. Cl.
*A61N 1/365* (2006.01)
(52) U.S. Cl. ............... 607/17; 607/18; 607/2
(58) Field of Classification Search ............ 607/17–19, 607/36, 119
See application file for complete search history.

(56) References Cited

U.S. PATENT DOCUMENTS

| | | | |
|---|---|---|---|
| 4,562,841 A | 1/1986 | Brockway et al. | |
| 4,784,162 A | 11/1988 | Ricks et al. | |
| 4,827,943 A | 5/1989 | Bornn et al. | |
| 4,953,551 A | 9/1990 | Mehra et al. | |
| 5,036,849 A | 8/1991 | Hauck et al. | |
| 5,133,353 A | 7/1992 | Hauser | |
| 5,170,784 A | 12/1992 | Ramon et al. | |
| 5,179,945 A | 1/1993 | Van Hofwegen et al. | |
| 5,203,348 A | 4/1993 | Dahl et al. | |
| 5,209,229 A | 5/1993 | Gilli | |
| 5,230,337 A | 7/1993 | Dahl et al. | |
| 5,261,400 A | 11/1993 | Bardy | |
| 5,284,136 A | 2/1994 | Hauck et al. | |
| 5,292,338 A | 3/1994 | Bardy | |
| 5,300,106 A | 4/1994 | Dahl et al. | |
| 5,301,677 A | 4/1994 | Hsung | |
| 5,313,953 A | 5/1994 | Yomtov et al. | |

(Continued)

FOREIGN PATENT DOCUMENTS

EP 0 488 512 A 6/1992

(Continued)

OTHER PUBLICATIONS

Renee Hartz et al., *New Approach to Defibrillator Insertion*, J. Thoracic Cardiovascular Surgery, vol. 97, pp. 920-922 (1989).

(Continued)

*Primary Examiner*—Robert E. Pezzuto
*Assistant Examiner*—Brian T. Gedeon
(74) *Attorney, Agent, or Firm*—Hollingsworth & Funk, LLC (57) ABSTRACT

A system includes a housing with energy delivery circuitry and detection circuitry. One or more electrodes are coupled to the circuitry and used to sense cardiac and muscle activity. A processor is coupled to the energy delivery and detection circuitry. The processor may detect a ventricular arrhythmia using a cardiac signal developed from the sensed cardiac activity and may also detect an activity state of the patient using an activity signal developed from the sensed muscle activity. The processor modifies delivery of a therapy to treat the arrhythmia in response to the activity signal. A method involves detecting signals using subcutaneous electrodes, and discerning a cardiac signal and a patient activity signal from the detected signals. Arrhythmia therapy may be modified to treat the arrhythmia in response to the activity signal.

35 Claims, 7 Drawing Sheets

U.S. PATENT DOCUMENTS

| | | |
|---|---|---|
| 5,314,430 A | 5/1994 | Bardy |
| 5,314,459 A | 5/1994 | Swanson et al. |
| 5,331,966 A | 7/1994 | Bennett et al. |
| 5,342,404 A | 8/1994 | Alt et al. |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,539 A | 5/1995 | Neisz |
| 5,417,714 A | 5/1995 | Levine et al. |
| 5,439,482 A | 8/1995 | Adams et al. |
| 5,441,518 A | 8/1995 | Adams et al. |
| 5,468,254 A | 11/1995 | Hahn et al. |
| 5,531,779 A | 7/1996 | Dahl et al. |
| 5,545,202 A | 8/1996 | Dahl et al. |
| 5,556,421 A | 9/1996 | Prutchi et al. |
| 5,603,732 A | 2/1997 | Dahl et al. |
| 5,606,969 A | 3/1997 | Butler et al. |
| 5,620,466 A | 4/1997 | Haefner et al. |
| 5,634,938 A | 6/1997 | Swanson et al. |
| 5,641,326 A | 6/1997 | Adams |
| 5,662,688 A | 9/1997 | Haefner et al. |
| 5,697,953 A | 12/1997 | Kroll et al. |
| 5,704,365 A | 1/1998 | Albrecht et al. |
| 5,724,984 A | 3/1998 | Arnold et al. |
| 5,827,326 A | 10/1998 | Kroll et al. |
| 5,895,414 A | 4/1999 | Sanchez-Zambrano |
| 5,916,243 A | 6/1999 | KenKnight et al. |
| 5,919,141 A | 7/1999 | Money et al. |
| 5,957,956 A | 9/1999 | Kroll et al. |
| 5,961,446 A | 10/1999 | Beller et al. |
| 5,961,450 A | 10/1999 | Merchant et al. |
| 6,044,298 A | 3/2000 | Salo et al. |
| 6,050,940 A | 4/2000 | Braun et al. |
| 6,055,454 A | 4/2000 | Heemels |
| 6,122,536 A | 9/2000 | Sun et al. |
| 6,144,879 A | 11/2000 | Gray |
| 6,148,230 A | 11/2000 | KenKnight |
| 6,198,952 B1 | 3/2001 | Miesel |
| 6,280,462 B1 | 8/2001 | Hauser et al. |
| 6,375,614 B1 | 4/2002 | Braun et al. |
| 6,409,675 B1 | 6/2002 | Turcott |
| 6,415,174 B1 | 7/2002 | Bebehani et al. |
| 6,438,410 B1 | 8/2002 | Hsu et al. |
| 6,454,708 B1 | 9/2002 | Ferguson et al. |
| 6,480,733 B1 | 11/2002 | Turcott |
| 6,491,639 B1 | 12/2002 | Turcott |
| 6,512,940 B1 | 1/2003 | Brabec et al. |
| 6,522,915 B1 | 2/2003 | Ceballos et al. |
| 6,564,106 B1 | 5/2003 | Guck et al. |
| 6,607,509 B1 | 8/2003 | Bobroff et al. |
| 6,615,083 B1 | 9/2003 | Kupper |
| 6,622,046 B1 | 9/2003 | Fraley et al. |
| 6,628,986 B1 | 9/2003 | Mouchawar et al. |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082658 A1 | 6/2002 | Heinrich et al. |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107552 A1 | 8/2002 | Gilkerson et al. |
| 2002/0107559 A1 | 8/2002 | Sanders et al. |
| 2002/0120299 A1 | 8/2002 | Ostroff et al. |
| 2002/0147474 A1 | 10/2002 | Morris et al. |
| 2003/0004546 A1 | 1/2003 | Casey |
| 2003/0004552 A1 | 1/2003 | Plombon et al. |
| 2003/0023175 A1 | 1/2003 | Arzbaecher et al.. |
| 2003/0036778 A1 | 2/2003 | Ostroff et al. |
| 2003/0045904 A1 | 3/2003 | Bardy et al. |
| 2003/0069609 A1 | 4/2003 | Thompson |
| 2003/0088278 A1 | 5/2003 | Bardy et al. |
| 2003/0088279 A1 | 5/2003 | Rissmann et al. |
| 2003/0088280 A1 | 5/2003 | Ostroff |
| 2003/0088281 A1 | 5/2003 | Ostroff et al. |
| 2003/0088282 A1 | 5/2003 | Ostroff |
| 2003/0088283 A1 | 5/2003 | Ostroff |
| 2003/0088286 A1 | 5/2003 | Ostroff et al. |
| 2003/0097153 A1 | 5/2003 | Bardy et al. |
| 2003/0212436 A1 | 11/2003 | Brown |

FOREIGN PATENT DOCUMENTS

| | | |
|---|---|---|
| WO | WO 92/20402 | 11/1992 |
| WO | WO 03/020367 A | 3/2003 |

OTHER PUBLICATIONS

Theofilos M. Kolettis, MD, PhD et al., *Submammary Implantation of a Cardioverter-Defibrillator with a Nonthoractomy Lead System*, Am. Heart J., vol. 126, pp. 1222-1223 (Nov. 1993).

John C. Schuder et al., *Transthoracic Ventricular Defibrillation in the Dog with Truncated and Untruncated Exponential Stimuli*, IEEE Trans. on Bio-Medical Engin., vol. BME-18, No. 6, pp. 410-415 (Nov. 1971).

John C. Schuder et al., *Ventricular Defibrillation in the Dog Using Implanted and Partially Implanted Electrode Systems*, Am. J. of Cardiology, vol. 33, pp. 243-247 (Feb. 1974).

John C. Schuder et al., *Experimental Ventricular Defibrillation with an Automatic and Completely Implanted System*, Trans. Am. Soc. Artif. Int. Organs, vol. 16, pp. 207-212 (1970).

Karel Smits & Marek Malik, *Defibrillation Threshold (DFT) Model of a Fully Subcutaneous ICD System*. Europace Supplements, vol. 2, Jun. 2001 at col. 778, p. 883.

Stirbis et al., *Optmizing the Shape of Implanted Artificial Pacemakers*, Kaunas Medical Institute. Translated from Meditsinskaya Tekhnika, No. 6, pp. 25-27 (1986).

Charles T. Leng et al., *Lead Configuration for Defibrillator Implantation in a Patient with Congenital Heart Disease and a Mechanical Prosthetic Tricuspid Valve*, PACE, vol. 24, No. 8, pp. 1291-1292 (Aug. 2001).

Park & Pollock, *Use of an Implantable Cardioverter Defibrillator in an Eight-Month-Old Infant with Ventricular Fibrillation Arising from a Myocardial Fibroma*, PACE, vol. 22, No. 1, pp. 138-139 (Jan. 1999).

Rainer Gradaus M.D. et al., *Nonthoracolomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360 (Mar. 2001).

SUBCUTANEOUS CARDIAC STIMULATION SYSTEM WITH PATIENT ACTIVITY SENSING

RELATED APPLICATIONS

This application claims the benefit of Provisional Patent Application Ser. No. 60/462,272, filed on Apr. 11, 2003, to which priority is claimed pursuant to 35 U.S.C. §119(e) and which is hereby incorporated herein by reference.

FIELD OF THE INVENTION

The present invention relates generally to implantable medical devices and, more particularly, to subcutaneous cardiac sensing and/or stimulation devices employing arrhythmia discrimination with patient activity sensing.

BACKGROUND OF THE INVENTION

The healthy heart produces regular, synchronized contractions. Rhythmic contractions of the heart are normally controlled by the sinoatrial (SA) node, which is a group of specialized cells located in the upper right atrium. The SA node is the normal pacemaker of the heart, typically initiating 60–100 heartbeats per minute. When the SA node is pacing the heart normally, the heart is said to be in normal sinus rhythm (NSR).

If the heart's electrical activity becomes uncoordinated or irregular, the heart is denoted to be arrhythmic. Cardiac arrhythmia impairs cardiac efficiency and may be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Typical Implantable cardioverter/defibrillators (ICDs) include one or more endocardial leads to which at least one defibrillation electrode is connected. Such ICDs are capable of delivering high-energy shocks to the heart, interrupting the ventricular tachyarrhythmia or ventricular fibrillation, and allowing the heart to resume normal sinus rhythm. ICDs may also include pacing functionality.

Although ICDs are very effective at preventing Sudden Cardiac Death (SCD), most people at risk of SCD are not provided with implantable defibrillators. Primary reasons for this unfortunate reality include the limited number of physicians qualified to perform transvenous lead/electrode implantation, a limited number of surgical facilities adequately equipped to accommodate such cardiac procedures, and a limited number of the at-risk patient population that may safely undergo the required endocardial or epicardial lead/electrode implant procedure.

SUMMARY OF THE INVENTION

The present invention is directed to cardiac monitoring and/or stimulation methods and systems that, in general, provide transthoracic monitoring, defibrillation therapies, pacing therapies, or a combination of these capabilities. Embodiments of the present invention are directed to subcutaneous cardiac monitoring and/or stimulation methods and systems that detect and/or treat cardiac activity or arrhythmias.

According to one embodiment of the invention, a medical system includes a housing with energy delivery circuitry and detection circuitry provided in the housing. One or more electrodes are coupled to the energy delivery and detection circuitry and used to sense cardiac and muscle activity. A processor is provided in the housing and coupled to the energy delivery and detection circuitry. The processor may detect a ventricular arrhythmia using a cardiac signal developed from the sensed cardiac activity and may also detect an activity state of the patient using an activity signal developed from the sensed muscle activity. The processor may modify delivery of a therapy to treat the arrhythmia in response to the muscle activity signal.

In another embodiment of the present invention, the processor inhibits delivery of the arrhythmia therapy in response to the activity signal exceeding an activity threshold, indicating patient consciousness or movement. The processor may inhibit delivery of the arrhythmia therapy for a predetermined time period in response to the activity signal exceeding an activity threshold, and withhold delivery of the arrhythmia therapy upon expiration of the predetermined time period and cessation of the arrhythmia. The processor may immediately deliver the arrhythmia therapy irrespective of the activity signal in response to detection of a life-threatening arrhythmia.

In another embodiment, the processor may receive an electrocardiogram from the detection circuitry and discriminate the cardiac signal and the activity signal from the electrocardiogram using an electrode arrangement configured for muscle signal detection.

A method in accordance with the present invention involves detecting signals using one or more electrodes, and discerning a cardiac signal from the detected signals. An activity signal associated with patient activity is also discerned from the detected signals. An arrhythmia may be detected using the cardiac signal and patient activity level may be detected using the activity signal. Arrhythmia therapy may be modified to treat the arrhythmia in response to the activity signal. Delivery of the arrhythmia therapy may be inhibited in response to the activity signal exceeding an activity threshold, using a signal indicating patient consciousness or movement. Delivery of the arrhythmia therapy may be inhibited for a predetermined time period in response to the activity signal exceeding an activity threshold, and delivery of the arrhythmia therapy may be withheld upon expiration of the predetermined time period and cessation of the arrhythmia.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a cardiac monitor or a cardiac stimulator may be implemented to include one or more of the advantageous features and/or processes described below. It is intended that such a monitor, stimulator, or other implanted or partially implanted device need not include all of the features described herein, but may be implemented to include selected features that provide for unique structures and/or functionality. Such a device may be implemented to provide a variety of therapeutic or diagnostic functions.

In general terms, combined cardiac signal detection and patient activity sensing arrangements and methods may be used with a subcutaneous cardiac monitoring and/or stimulation device. One such device is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more leads incorporating electrodes may be located in direct contact with the heart, great vessel or coronary vasculature, such as via one or more leads implanted by use of conventional transvenous delivery approaches. In a further implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

Certain configurations illustrated herein are generally capable of implementing various functions traditionally performed by an ICD, and may operate in numerous cardioversion/defibrillation modes as are known in the art. Exemplary ICD circuitry, structures and functionality, aspects of which may be incorporated in an ITCS device of a type that may benefit from patient activity sensing in accordance with the present invention, are disclosed in commonly owned U.S. Pat. Nos. 5,133,353; 5,179,945; 5,314,459; 5,318,597; 5,620,466; and 5,662,688, which are hereby incorporated herein by reference in their respective entireties.

In particular configurations, systems and methods may perform functions traditionally performed by pacemakers, such as providing various pacing therapies as are known in the art, in addition to cardioversion/defibrillation therapies. Exemplary pacemaker circuitry, structures and functionality, aspects of which may be incorporated in an ITCS device of a type that may benefit from patient activity sensing are disclosed in commonly owned U.S. Pat. Nos. 4,562,841; 5,284,136; 5,376,106; 5,036,849; 5,540,727; 5,836,987;

6,044,298; and 6,055,454, which are hereby incorporated herein by reference in their respective entireties. It is understood that ITCS device configurations may provide for non-physiologic pacing support in addition to, or to the exclusion of, bradycardia and/or anti-tachycardia pacing therapies.

An ITCS device in accordance with the present invention may implement diagnostic and/or monitoring functions as well as provide cardiac stimulation therapy. Exemplary cardiac monitoring circuitry, structures and functionality, aspects of which may be incorporated in an ITCS device of a type that may benefit from information on patient activity in accordance with the present invention, are disclosed in commonly owned U.S. Pat. Nos. 5,313,953; 5,388,578; and 5,411,031, which are hereby incorporated herein by reference.

An ITCS device may be used to implement various diagnostic functions, which may involve performing rate-based, pattern and rate-based, and/or morphological tachyarrhythmia discrimination analyses. Subcutaneous, cutaneous, and/or external sensors may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

Figure 1A:
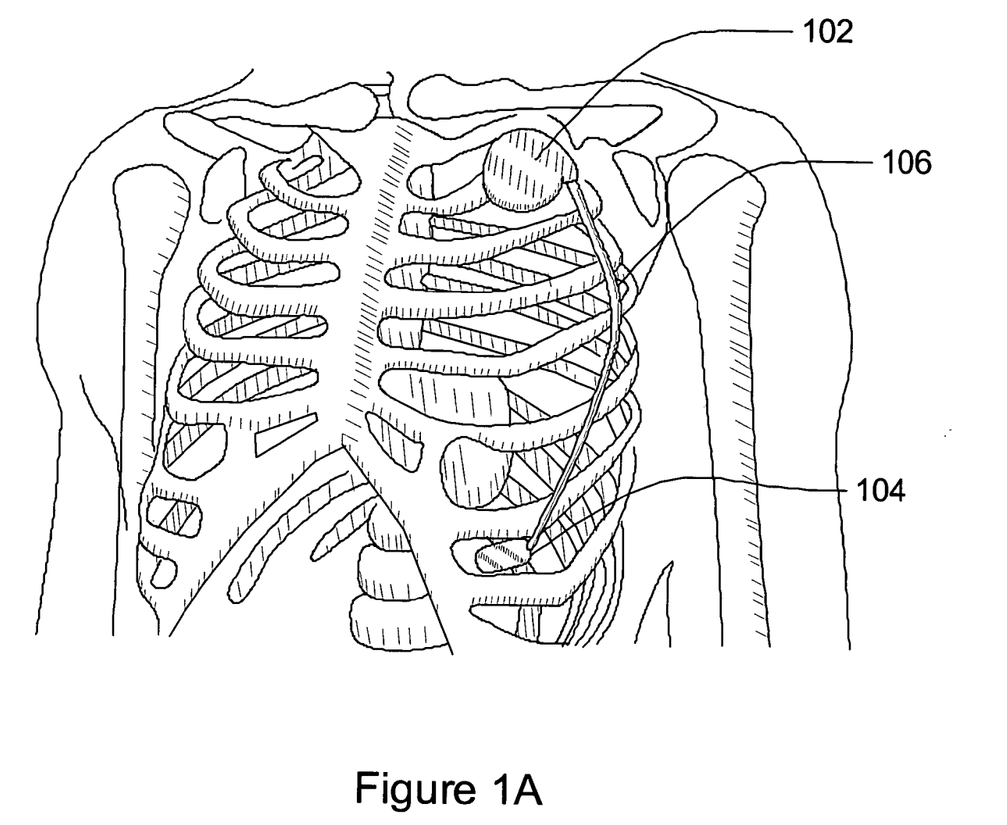
FIGS. 1A and 1B are views of a transthoracic cardiac sensing and/or stimulation device as implanted in a patient in accordance with an embodiment of the present invention.
Figure 1B:
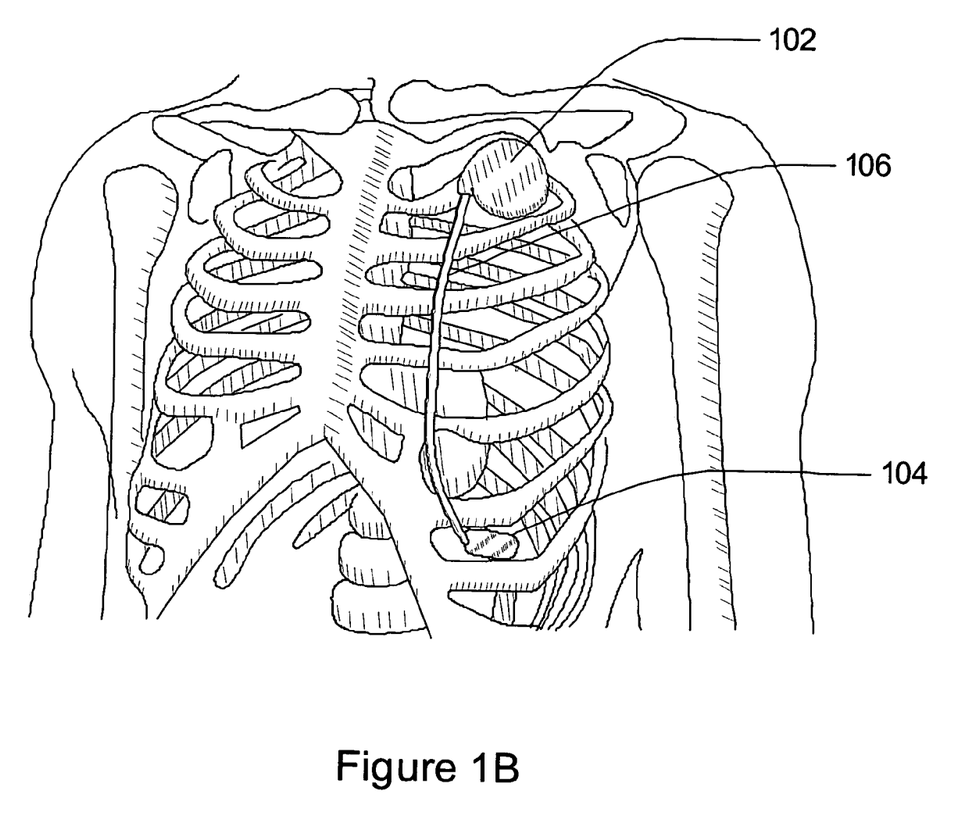

Referring now to FIGS. 1A and 1B of the drawings, there is shown a configuration of an ITCS device with components implanted in the chest region of a patient at different locations. In the particular configuration shown in FIGS. 1A and 1B, the ITCS device includes a housing 102 within which various cardiac sensing, detection, processing, and energy delivery circuitry may be housed. It is understood that the components and functionality depicted in the figures and described herein may be implemented in hardware, software, or a combination of hardware and software. It is further understood that the components and functionality depicted as separate or discrete blocks/elements in the figures may be implemented in combination with other components and functionality, and that the depiction of such components and functionality in individual or integral form is for purposes of clarity of explanation, and not of limitation.

Communications circuitry is disposed within the housing 102 for facilitating communication between the ITCS device and an external communication device, such as a portable or bed-side communication station, patient-carried/worn communication station, or external programmer, for example. The communications circuitry may also facilitate unidirectional or bidirectional communication with one or more external, cutaneous, or subcutaneous physiologic or non-physiologic sensors. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed.

In the configuration shown in FIGS. 1A and 1B, a subcutaneous electrode 104 may be positioned under the skin in the chest region and situated distal from the housing 102. The subcutaneous and, if applicable, housing electrode(s) may be positioned about the heart at various locations and orientations, such as at various anterior and/or posterior locations relative to the heart. The subcutaneous electrode 104 is coupled to circuitry within the housing 102 via a lead assembly 106. One or more conductors (e.g., coils or cables) are provided within the lead assembly 106 and electrically couple the subcutaneous electrode 104 with circuitry in the housing 102. One or more sense, sense/pace or defibrillation electrodes may be situated on the elongated structure of the electrode support, the housing 102, and/or the distal electrode assembly (shown as subcutaneous electrode 104 in the configuration shown in FIGS. 1A and 1B).

The electrode support assembly defines a physically separable unit relative to the housing 102. The electrode support assembly includes mechanical and electrical couplings that facilitate mating engagement with corresponding mechanical and electrical couplings of the housing 102. For example, a header block arrangement may be configured to include both electrical and mechanical couplings that provide for mechanical and electrical connections between the electrode support assembly and housing 102. The header block arrangement may be provided on the housing 102 or the electrode support assembly. Alternatively, a mechanical/electrical coupler may be used to establish mechanical and electrical connections between the electrode support assembly and housing 102. In such a configuration, a variety of different electrode support assemblies of varying shapes, sizes, and electrode configurations may be made available for physically and electrically connecting to a standard ITCS device housing 102.

It is noted that the electrodes 104 and the lead assembly 106 may be configured to assume a variety of shapes. For example, the lead assembly 106 may have a wedge, chevron, flattened oval, or a ribbon shape, and the subcutaneous electrode 104 may include a number of spaced electrodes, such as an array or band of electrodes. Moreover, two or more subcutaneous electrodes 104 may be mounted to multiple electrode support assemblies 106 to achieve a desired spaced relationship amongst subcutaneous electrodes 104.

An ITCS device may incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243, which are hereby incorporated herein by reference in their respective entireties.

Figure 1C:
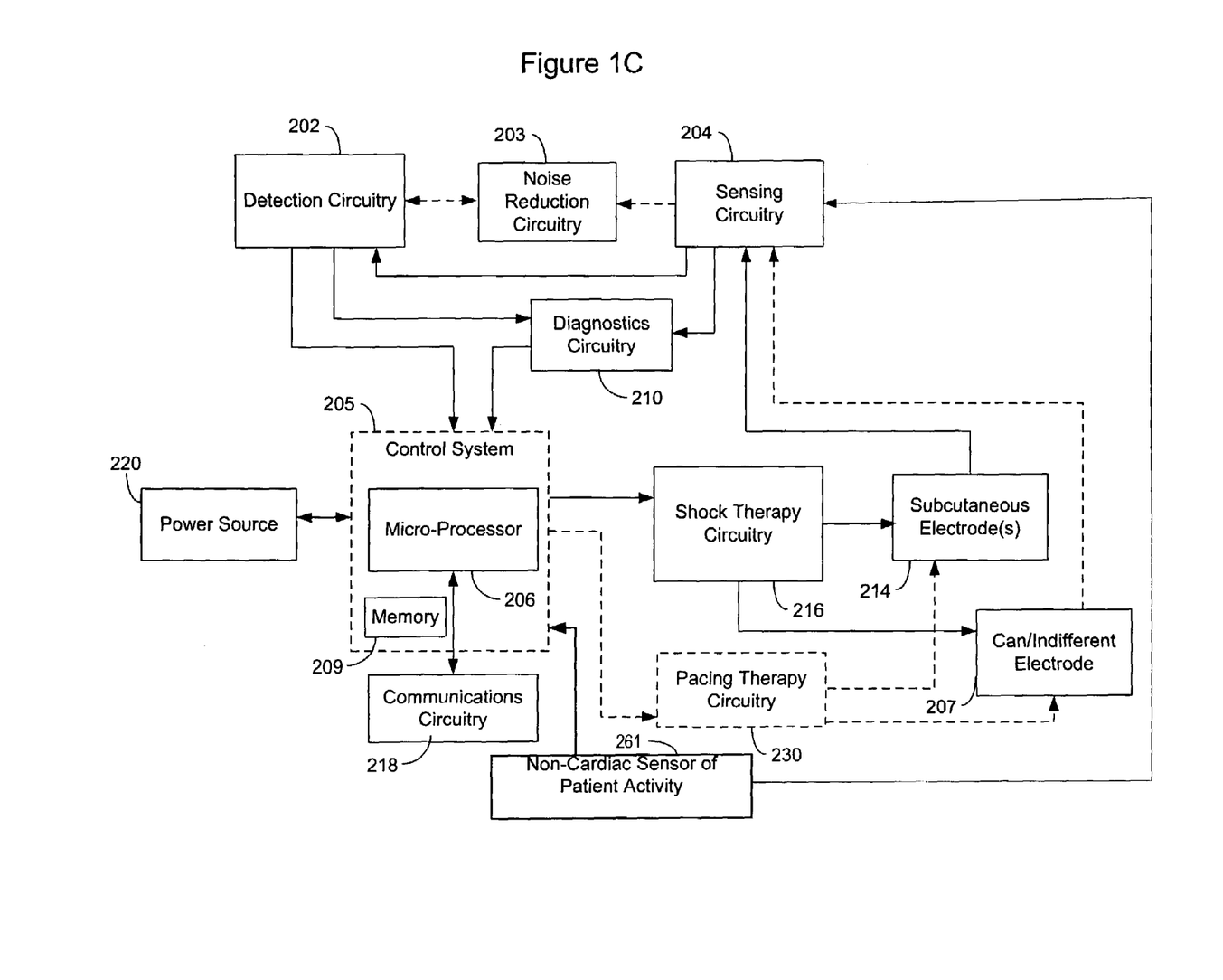
FIG. 1C is a block diagram illustrating various components of a transthoracic cardiac sensing and/or stimulation device in accordance with an embodiment of the present invention.

FIG. 1C is a block diagram depicting various components of an ITCS device in accordance with one configuration. According to this configuration, the ITCS device incorporates a processor-based control system 205 which includes a microprocessor 206 coupled to appropriate memory (volatile and/or non-volatile) 209, it being understood that any logic-based control architecture may be used. The control system 205 is coupled to circuitry and components to sense, detect, and analyze electrical signals produced by the heart and patient activity signals. The control system 205 is also configured to deliver electrical stimulation energy to the heart under predetermined conditions to treat cardiac arrhythmias. In certain configurations, the control system 205 and associated components also provide pacing therapy to the heart. The electrical energy delivered by the ITCS device may be in the form of low energy pacing pulses or high-energy pulses for cardioversion or defibrillation.

Electrocardiogram (ECG) signals and skeletal muscle signals are sensed using the subcutaneous electrode(s) 214 and/or the can or indifferent electrode 207 provided on the ITCS device housing. ECG and skeletal muscle signals may also be sensed using only the subcutaneous electrodes 214, such as in a non-active can configuration. As such, unipolar, bipolar, or combined unipolar/bipolar electrode configurations as well as multi-element electrodes and combinations of noise canceling and standard electrodes may be employed. The sensed ECG signals are received by sensing circuitry 204, which includes sense amplification circuitry and may also include filtering circuitry and an analog-to-digital (A/D) converter. The sensed ECG and skeletal muscle signals processed by the sensing circuitry 204 may be received by noise reduction circuitry 203, which may further reduce noise before signals are sent to the detection circuitry 202.

Noise reduction circuitry 203 may also be incorporated after detection circuitry 202 in cases where high power or computationally intensive noise reduction algorithms are required. The noise reduction circuitry 203, by way of amplifiers used to perform operations with the electrode signals, may also perform the function of the sensing circuitry 204. Combining the functions of sensing circuitry 204 and noise reduction circuitry 203 may be useful to minimize the necessary componentry and lower the power requirements of the system.

In the illustrative configuration shown in FIG. 1C, the detection circuitry 202 is coupled to, or otherwise incorporates, noise reduction circuitry 203. The noise reduction circuitry 203 operates to improve the signal-to-noise ratio of sensed signals by removing noise content of the sensed cardiac signals introduced from various sources.

Detection circuitry 202 typically includes a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 202 to detect and verify the presence and severity of an arrhythmic episode. Exemplary arrhythmia detection and discrimination circuitry, structures, and techniques, aspects of which may be implemented by an ITCS device of a type that may benefit from patient activity sensing in accordance with the present invention, are disclosed in commonly owned U.S. Pat. Nos. 5,301,677 and 6,438,410, which are hereby incorporated herein by reference in their respective entireties. In another example of arrhythmia detection using the detection circuitry 202, two or more electrodes are sensed by the processor individually. The processor may detect arrhythmias using one or more sensed activation sequences over the two or more electrodes. The activation sequences may contain information sufficient to detect or discriminate cardiac arrhythmias.

The detection circuitry 202 communicates cardiac signal information to the control system 205. Memory circuitry 209 of the control system 205 contains parameters for operating in various sensing, defibrillation, and, if applicable, pacing modes, and stores data indicative of cardiac signals received by the detection circuitry 202. The memory circuitry 209 may also be configured to store historical ECG and therapy data, which may be used for various purposes and transmitted to an external receiving device as needed or desired.

In certain configurations, the ITCS device may include diagnostics circuitry 210. The diagnostics circuitry 210 typically receives input signals from the detection circuitry 202 and the sensing circuitry 204. The diagnostics circuitry 210 provides diagnostics data to the control system 205, it being understood that the control system 205 may incorporate all or part of the diagnostics circuitry 210 or its functionality. The control system 205 may store and use information provided by the diagnostics circuitry 210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 205 processes cardiac signal data received from the detection circuitry 202 and initiates appropriate tachyarrhythmia therapies to terminate cardiac arrhythmic episodes and return the heart to normal sinus rhythm. The control system 205 is coupled to shock therapy circuitry 216. The shock therapy circuitry 216 is coupled to the subcutaneous electrode(s) 214 and the can or indifferent electrode 207 of the ITCS device housing. Upon command, the shock therapy circuitry 216 delivers cardioversion and defibrillation stimulation energy to the heart in accordance with a selected cardioversion or defibrillation therapy. In a less sophisticated configuration, the shock therapy circuitry 216 is controlled to deliver defibrillation therapies, in contrast to a configuration that provides for delivery of both cardioversion and defibrillation therapies. Examples of ICD high energy delivery circuitry, structures and functionality, aspects of which may be incorporated in an ITCS device in accordance with the present invention are disclosed in commonly owned U.S. Pat. Nos. 5,372,606; 5,411,525; 5,468,254; and 5,634,938, which are hereby incorporated herein by reference.

In accordance with another configuration, an ITCS device may incorporate a cardiac pacing capability in addition to cardioversion and/or defibrillation capabilities. As is shown in dotted lines in FIG. 1C, the ITCS device may include pacing therapy circuitry 230, which is coupled, to the control system 205 and the subcutaneous and can/indifferent electrodes 214, 207. Upon command, the pacing therapy circuitry delivers pacing pulses to the heart in accordance with a selected pacing therapy. Control signals, developed in accordance with a pacing regimen by pacemaker circuitry within the control system 205, are initiated and transmitted to the pacing therapy circuitry 230 where pacing pulses are generated.

A number of cardiac pacing therapies may be useful in a transthoracic cardiac monitoring and/or stimulation device. Such cardiac pacing therapies may be delivered via the pacing therapy circuitry 230 as shown in FIG. 1C. Alternatively, cardiac pacing therapies may be delivered via the shock therapy circuitry 216, which effectively obviates the need for separate pacemaker circuitry.

The ITCS device shown in FIG. 1C is configured to receive signals from one or more physiologic and/or non-physiologic sensors used to sense patient activity in accordance with embodiments of the present invention. Depending on the type of sensor employed, signals generated by the sensors may be communicated to transducer circuitry coupled directly to the detection circuitry 202 or indirectly via the sensing circuitry 204. It is noted that certain sensors may transmit sense data to the control system 205 without processing by the detection circuitry 202.

Non-cardiac sensors may be coupled directly to the detection circuitry 202 or indirectly via the sensing circuitry 204. One or more non-cardiac sensors sense patient activity, such as movement, walking, or other indications the patient is performing normal activities during consciousness. Examples of non-cardiac sensors are skeletal muscle specific electrodes, electromyogram sensors, acoustic sensors and/or pressure transducers, and accelerometers. Signals from these sensors may be used to detect patient activity, such as movement, position, or the like. A non-cardiac sensor 261 is illustrated in FIG. 1C connected to one or both of the sensing circuitry 204 and the control system 205.

Communications circuitry 218 is coupled to the microprocessor 206 of the control system 205. The communications circuitry 218 allows the ITCS device to communicate with one or more receiving devices or systems situated external to the ITCS device. By way of example, the ITCS device may communicate with a patient-worn, portable or bedside communication system via the communications circuitry 218. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the ITCS device via the communications circuitry 218. It is noted that physiologic or non-physiologic sensors equipped with wireless transmitters or transceivers may communicate with a receiving system external of the patient.

The communications circuitry 218 may allow the ITCS device to communicate with an external programmer. In one configuration, the communications circuitry 218 and the programmer unit (not shown) use a wire loop antenna and a radio frequency telemetric link, as is known in the art, to receive and transmit signals and data between the programmer unit and communications circuitry 218. In this manner, programming commands and data are transferred between the ITCS device and the programmer unit during and after implant. Using a programmer, a physician is able to set or modify various parameters used by the ITCS device. For example, a physician may set or modify parameters affecting sensing, detection, pacing, and defibrillation functions of the ITCS device, including pacing and cardioversion/defibrillation therapy modes.

Typically, the ITCS device is encased and hermetically sealed in a housing suitable for implanting in a human body as is known in the art. Power to the ITCS device is supplied by an electrochemical power source 220 housed within the ITCS device. In one configuration, the power source 220 includes a rechargeable battery. According to this configuration, charging circuitry is coupled to the power source 220 to facilitate repeated non-invasive charging of the power source 220. The communications circuitry 218, or separate receiver circuitry, is configured to receive radio-frequency (RF) energy transmitted by an external RF energy transmitter. The ITCS device may, in addition to a rechargeable power source, include a non-rechargeable battery. It is understood that a rechargeable power source need not be used, in which case a long-life non-rechargeable battery is employed.

Figure 1D:
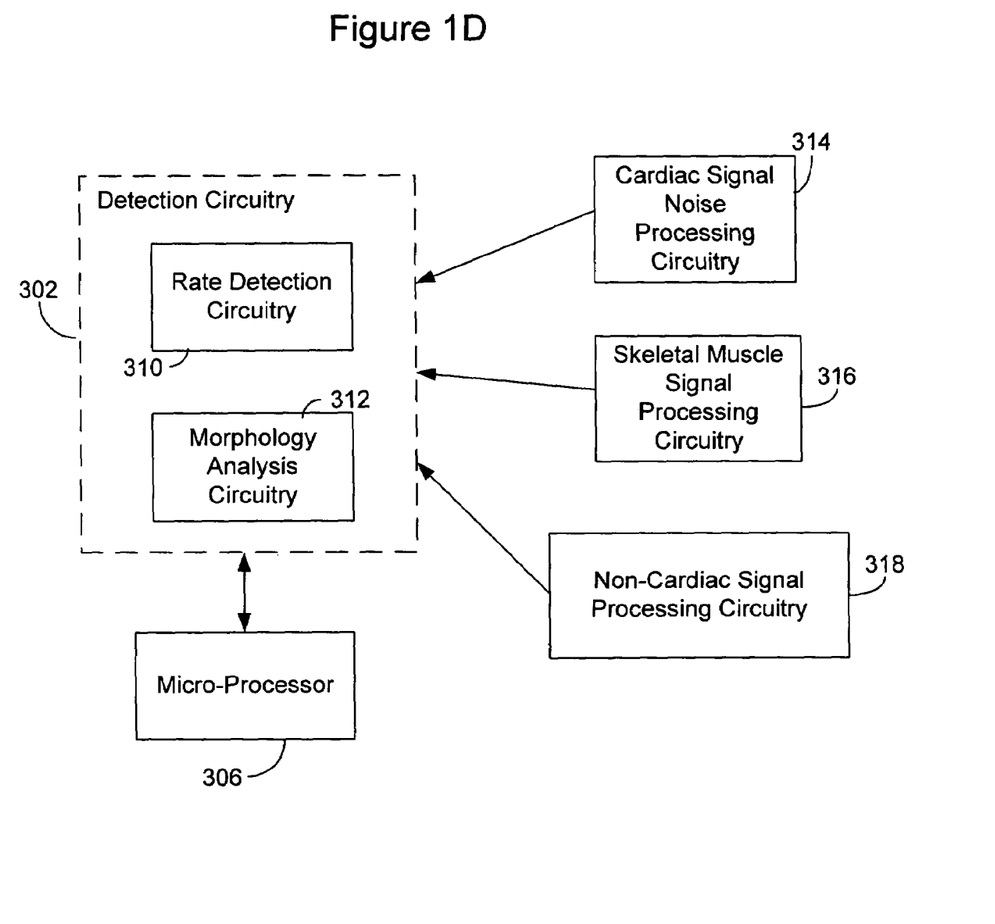
FIG. 1D is a block diagram illustrating various processing and detection components of a transthoracic cardiac sensing and/or stimulation device in accordance with an embodiment of the present invention.

FIG. 1D illustrates a configuration of detection circuitry 302 of an ITCS device, which includes one or both of rate detection circuitry 310 and morphological analysis circuitry 312. Detection and verification of arrhythmias may be accomplished using rate-based discrimination algorithms as known in the art implemented by the rate detection circuitry 310. Arrhythmic episodes may also be detected and verified by morphology-based analysis of sensed cardiac signals as is known in the art. For example, ECG signal curvature, inflection points, amplitudes, and relationships between morphologic features may be used to detect and/or verify cardiac arrhythmias. Tiered or parallel arrhythmia discrimination algorithms may also be implemented using both rate-based and morphologic-based approaches. Further, a rate and pattern-based arrhythmia detection and discrimination approach may be employed to detect and/or verify arrhythmic episodes, such as the approaches described in U.S. Pat. Nos. 6,487,443; 6,259,947; 6,141,581; 5,855,593; and 5,545,186, which are hereby incorporated herein by reference in their respective entireties.

The detection circuitry 302, which is coupled to a microprocessor 306, may be configured to incorporate, or communicate with, specialized circuitry for processing sensed signals in manners particularly useful in a transthoracic cardiac sensing and/or stimulation device. As is shown by way of example in FIG. 1D, the detection circuitry 302 may receive information from multiple physiologic and non-physiologic sensors.

Non-electrophysiological signals, such as from accelerometers, position sensors, movement sensors, or other patient activity monitoring sensors, may be detected and processed by non-electrophysiological activity signal processing circuitry 318 for a variety of purposes. The signals are transmitted to the detection circuitry 302, via a hardwire or wireless link, and may be used to enhance discrimination of arrhythmias from normal sinus rhythm.

Because the additional discriminating non-electrophysiologic signal is time correlated with respect to the cardiac electrophysiological signals, the non-electrophysiologic signal may provide information about a patient's rhythm state even in the presence of electrical noise and/or electrocardiographic artifacts. For example, the non-electrophysiologic signal may be used to verify that the ECG signal contains a cardiac signal having a QRS complex, and only ECG signals with QRS complexes are verified ECG signals. Subsequent analysis may require that only verified ECG signals are used for calculations of, for example, heart rate. This provides for more robust algorithms that are less susceptible to contamination from electrical interference and noise.

The detection circuitry 302 may also receive patient activity information from one or more sensors that monitor patient activity, such as electromyogram signals. In addition to ECG signals, transthoracic electrodes readily detect skeletal muscle signals. Such skeletal muscle signals may be used in accordance with the present invention to determine the activity level of the patient. Processing circuitry 316 receives signals from one or more patient activity sensors, and transmits processed patient activity signal data to the detection circuitry 302. This data may be used to enhance discrimination of arrhythmias from normal sinus rhythm in accordance with the present invention. Non-electrophysiological signals may be combined with muscle activity signals to provide additional signal information useful in performing cardiac rhythm monitoring, detection, evaluation, discrimination, treatment, and withholding of arrhythmia therapy. The use of non-electrophysiological signal information to discriminate arrhythmias is further described in commonly assigned U.S. patent application Ser. No. 10/804,471, filed Mar. 19, 2004, entitled "Multi-Parameter Arrhythmia Discrimination,", which is hereby incorporated herein by reference.

In accordance with embodiments of the invention, an ITCS device may be implemented to include a subcutaneous electrode system that provides for one or both of cardiac sensing and arrhythmia therapy delivery in combination with patient activity sensing, such as skeletal muscle signal sensing. According to one approach, an ITCS device may be implemented as a chronically implantable system that performs monitoring, diagnostic and/or therapeutic functions. The ITCS device may automatically detect and treat cardiac arrhythmias. In one configuration, the ITCS device includes a pulse generator and one or more electrodes that are implanted subcutaneously in the chest region of the body, such as in the anterior thoracic region of the body. The ITCS device may be used to provide atrial and ventricular therapy for bradycardia and/or tachycardia arrhythmias. Tachyarrhythmia therapy may include cardioversion, defibrillation and anti-tachycardia pacing (ATP), for example, to treat atrial or ventricular tachycardia or fibrillation. Bradycardia therapy may include temporary post-shock pacing for bradycardia or asystole. Methods and systems for implementing post-shock pacing for bradycardia or asystole are described in commonly assigned U.S. Patent Application entitled "Subcutaneous Cardiac Stimulator Employing Post-Shock Transthoracic Asystole Prevention Pacing", Ser. No. 10/377,274, filed on Feb. 28, 2003, which is incorporated herein by reference in its entirety.

In one configuration, an ITCS device according to one approach may utilize conventional pulse generator and subcutaneous electrode implant techniques. The pulse generator device and electrodes may be chronically implanted subcutaneously. Such an ITCS device may be used to automatically detect and treat arrhythmias similarly to conventional implantable systems. In another configuration, the ITCS device may include a unitary structure (e.g., a single housing/unit). The electronic components and electrode conductors/connectors are disposed within or on the unitary ITCS device housing/electrode support assembly.

The ITCS device contains the electronics and may be similar to a conventional implantable defibrillator. High voltage shock therapy may be delivered between two or more electrodes, one of which may be the pulse generator housing (e.g., can), placed subcutaneously in the thoracic region of the body.

Additionally or alternatively, the ITCS device may also provide lower energy electrical stimulation for bradycardia therapy. The ITCS device may provide brady pacing similarly to a conventional pacemaker. The ITCS device may provide temporary post-shock pacing for bradycardia or asystole. Sensing and/or pacing may be accomplished using sense/pace electrodes positioned on an electrode subsystem also incorporating shock electrodes, or by separate electrodes implanted subcutaneously.

The ITCS device may detect a variety of physiological signals that may be used in connection with various diagnostic, therapeutic or monitoring implementations. For example, the ITCS device may include sensors or circuitry for detecting respiratory system signals, cardiac system signals, and signals related to patient activity. In one embodiment, the ITCS device senses intrathoracic impedance, from which various respiratory parameters may be derived, including, for example, respiratory tidal volume and minute ventilation. Sensors and associated circuitry may be incorporated in connection with an ITCS device for detecting one or more body movement or body position related signals. For example, accelerometers and GPS devices may be employed to detect patient activity, patient location, body orientation, or torso position.

The ITCS device may be used within the structure of an advanced patient management (APM) system. Advanced patient management systems may allow physicians to remotely and automatically monitor cardiac and respiratory functions, as well as other patient conditions. In one example, implantable cardiac rhythm management systems, such as cardiac pacemakers, defibrillators, and resynchronization devices, may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

An ITCS device according to one approach provides an easy to implant therapeutic, diagnostic or monitoring system. The ITCS system may be implanted without the need for intravenous or intrathoracic access, providing a simpler, less invasive implant procedure and minimizing lead and surgical complications. In addition, this system would have advantages for use in patients for whom transvenous lead systems cause complications. Such complications include, but are not limited to, surgical complications, infection, insufficient vessel patency, complications associated with the presence of artificial valves, and limitations in pediatric patients due to patient growth, among others. An ITCS system according to this approach is distinct from conventional approaches in that it may be configured to include a combination of two or more electrode subsystems that are implanted subcutaneously in the anterior thorax.

Figure 2:
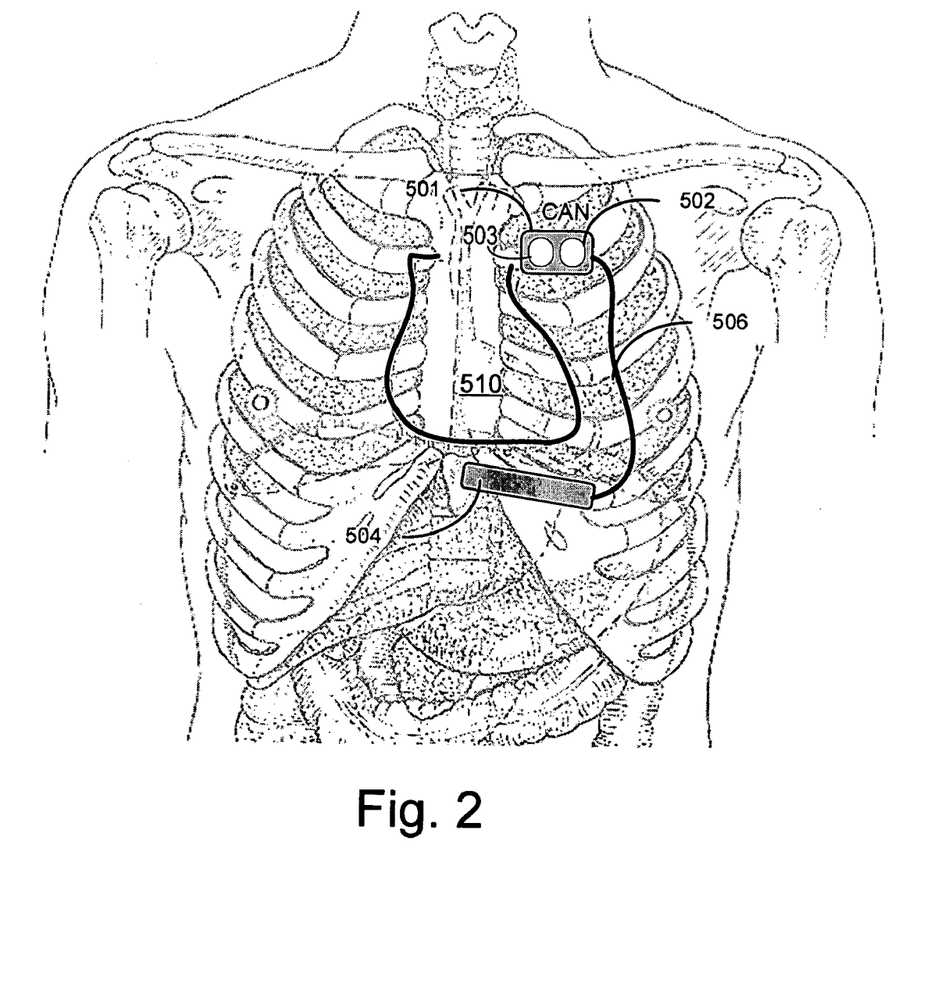
FIG. 2 is a diagram illustrating components of a transthoracic cardiac sensing and/or stimulation device as implanted in a patient in accordance with an embodiment of the present invention.

In one configuration, as is illustrated in FIG. 2, electrode subsystems of an ITCS system are arranged about a patient's heart 510. The ITCS system includes a first electrode subsystem 502, including a can electrode configured for the sensing of skeletal muscle activity, and a second electrode subsystem 504 that includes one or more electrodes. The electrode subsystems 502, 504 may include a number of electrodes used for sensing and/or electrical stimulation.

In various configurations, the second electrode subsystem 504 may include a combination of electrodes. The combination of electrodes of the second electrode subsystem 504 may include coil electrodes, tip electrodes, ring electrodes, multi-element coils, spiral coils, spiral coils mounted on non-conductive backing, screen patch electrodes, and other electrode configurations. A suitable non-conductive backing material is silicone rubber, for example.

The first electrode subsystem 502 is positioned on the housing 501 that encloses the ITCS device electronics. In one embodiment, the first electrode subsystem 502 includes the entirety of the external surface of housing 501. In other embodiments, various portions of the housing 501 may be electrically isolated from the first electrode subsystem 502 or from tissue. For example, the active area of the first electrode subsystem 502 may include all or a portion of either the anterior or posterior surface of the housing 501 to direct current flow in a manner advantageous for sensing cardiac activity, sensing skeletal muscle activity, and/or providing cardiac stimulation therapy. In another embodiment, the anterior facing portion of the can is isolated for skeletal muscle signal detection and the posterior facing portion of the can is isolated for ECG signal sensing.

In accordance with one embodiment, the housing 501 may resemble that of a conventional implantable ICD, is approximately 20–100 cc in volume, with a thickness of 0.4 to 2 cm and with a surface area on each face of approximately 30 to 100 $cm^2$. As previously discussed, portions of the housing may be electrically isolated from tissue to optimally direct current flow and/or provide shielding for specific sensing directivity. For example, portions of the housing 501 may be covered with a non-conductive, or otherwise electrically resistive, material to direct current flow. Suitable non-conductive material coatings include those formed from silicone rubber, polyurethane, or parylene, for example.

As was discussed above, cardiac signals collected from subcutaneously implanted electrodes may be corrupted by noise. In addition, certain noise sources have frequency characteristics similar to those of the cardiac signal. Such noise may lead to over sensing and spurious shocks. Due to the possibility of relatively high amplitude of the noise signal and overlapping frequency content, filtering alone does not lead to complete suppression of the noise. In addition, filter performance is not generally sufficiently robust against the entire class of noises encountered. Further, known adaptive filtering approaches require a reference signal that is often unknown for situations when a patient experiences ventricular fibrillation or high amplitude noise.

Subcutaneous cardiac sensing and/or stimulation devices may employ cardiac signal separation, which may be used to separate signals to discriminate a signal of interest within the separated signals, such as a skeletal muscle signal. Signal separation techniques provide for separation of many individual signals from composite signals. For example, a composite signal may contain several cardiac signals, skeletal muscle movement related signals, electromagnetic interference signals, and signals of unknown origin. Signal separation techniques separate the composite signal into individual signals. Devices and methods of blind source separation are further described in commonly owned U.S. patent application Ser. No. 10/741,814, filed Dec. 19, 2003, hereby incorporated herein by reference. Devices and methods of signal separation using noise canceling electrodes are further described in commonly owned U.S. patent application Ser. No. 10/738,608, filed Dec. 17, 2003, hereby incorporated herein by reference.

Figure 3:
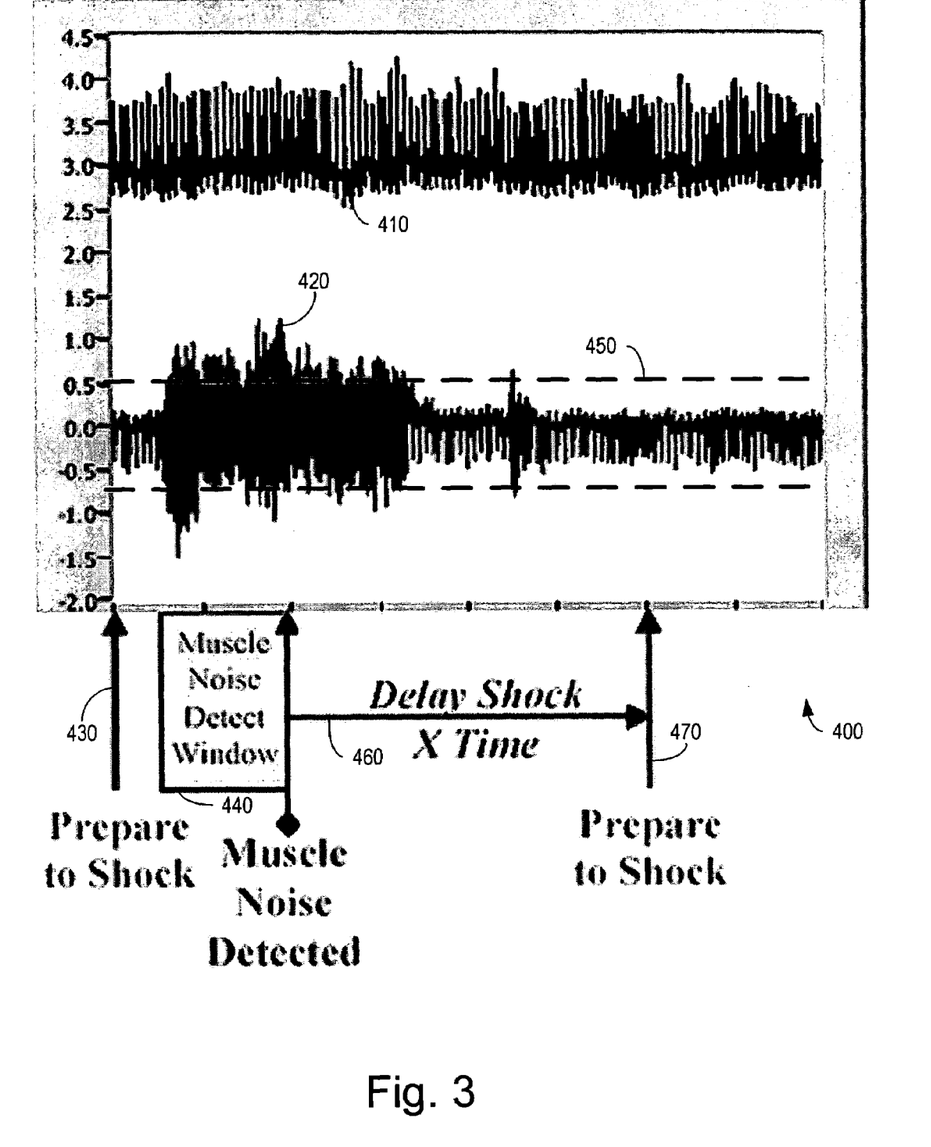
FIG. 3 is a graph of an electrocardiogram signal and a skeletal muscle signal including a threshold in accordance with an embodiment of the present invention.

FIG. 3 is a graph showing an electrocardiogram 410 and a patient activity signal 420, including a threshold 450, in accordance with an embodiment of the present invention. The graph includes time as its abscissa and signal voltage level as its ordinate. The ECG signal 410 and the patient activity signal 420 shown in FIG. 3 have been amplified and filtered. In this example, both the ECG signal 410 and the patient activity signal 420 are derived from cardiac electrodes. The patient activity signal 420 is, in this case, derived from a cardiac electrode arrangement preferentially located to provide a signal indicative of skeletal muscle activity. Note that the patient activity signal 420 includes a significant ECG component, but that muscle movement is clearly identifiable within at least a muscle noise detect window 440.

Muscle movement, indicative of a conscious and active patient, may be defined, for example, when the patient activity signal 420 exceeds the threshold 450. The threshold 450 may be adaptable, dynamic or fixed, and may be defined as an absolute value, as a percentage of a baseline, or using other known signal morphological or statistical methodologies. If, for example, the ECG signal 410 indicates an arrhythmia is occurring necessitating a shock to the patient, but the patient activity signal 420 indicates that the patient is mobile or active, then an algorithm in the ITCS device may delay shock to the patient's heart for a period of time, such as a delay 460.

The delay 460 provides a period of time during which the ITCS device evaluates whether there is a spurious signal in the ECG signal 410, or whether there is actually a need to shock the patient. The duration of the delay 460 is selected to provide the ITCS device additional time following initial detection of an arrhythmia to confirm the presence of the detected arrhythmia using one or more non-cardiac signals, such as skeletal muscle signals or patient movement signals. The delay period 460 should be sufficient in duration to allow for re-evaluation of the detected arrhythmia, while not compromising patient wellbeing. The duration of the delay 460 may range from 2 seconds to 60 seconds, for example. The device may also provide notification when the delay time is invoked.

After the delay 460, the ITCS device may begin charging the defibrillation capacitor(s) in preparation for delivering a shock to the patient, and may re-evaluate the patient activity signal 420 prior to delivering the shock. The patient activity signal 420 is re-evaluated to determine the activity status of the patient prior to delivering the shock at shock time 470.

At the shock time 470 shown in the graph in FIG. 3, the patient activity signal 420 has fallen below the threshold 450, indicating that the patient is no longer active. This may be because the patient has succumbed to insufficient blood supply, and is possibly unconscious. Clearly, the shock 470 is indicated, and is delivered to resuscitate the patient in this case. If, however, the ECG signal 410 at the shock time 470 indicates that the arrhythmia has terminated, a shock is not delivered to the patient, irrespective of the status of the patient activity signal 420.

The delay 460 may be used in a hierarchical manner, such that it is selectively used depending on the severity of the detected arrhythmia. For example, if the ECG signal 410 clearly indicates presence of a dangerous or life-threatening arrhythmia, then the delay 460 may be bypassed and the patient may be shocked immediately. If, however, the ECG signal 410 is inconclusive, but indicates a possibility of arrhythmia, then delivery of an arrhythmia therapy is delayed so that the patient activity signal 420 may be evaluated.

Figure 4:
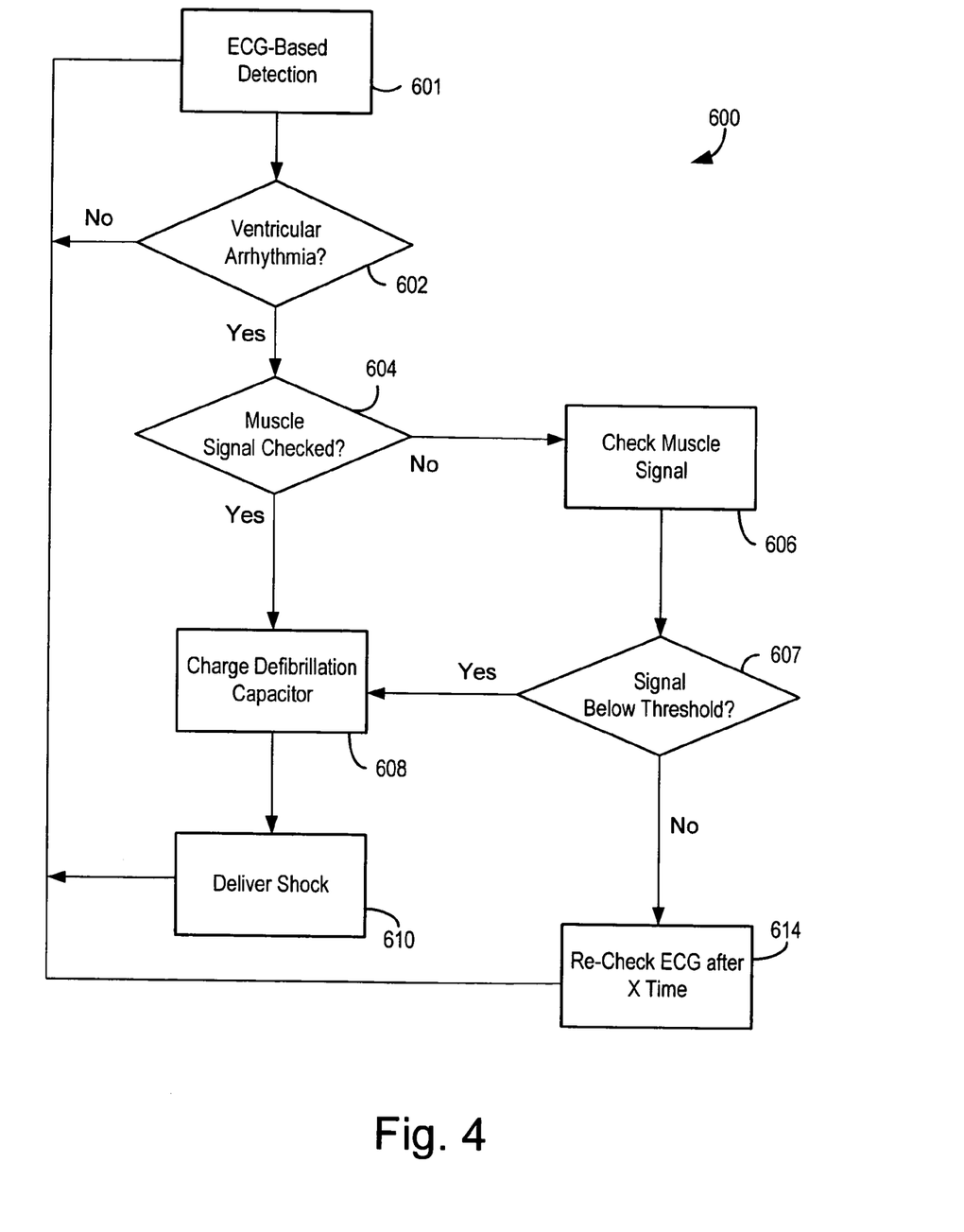
FIG. 4 is a flow chart of a method of arrhythmia discrimination in accordance with an embodiment of the present invention.

FIG. 4 illustrates various processes associated with one method of utilizing subcutaneous skeletal muscle signal detection in combination with ECG- or EGM-based rhythm detection. The skeletal muscle signal detection circuitry may be enabled after other means of arrhythmia detection have been utilized, such as cardiac electrogram-based algorithms. To conserve energy, for example, skeletal muscle signal detection may be activated after detecting an arrhythmia using cardiac signal detection circuitry, and thereafter deactivated after delivering an arrhythmia therapy or cessation of the arrhythmia. Discriminating arrhythmia event from noise using skeletal muscle signal detection in this manner can reduce occurrences of inappropriate shock delivery and offers the potential to significantly improve patient comfort.

With continued reference to FIG. 4, an ECG-based detection algorithm 600 is employed to detect cardiac arrhythmias in accordance with an embodiment of the invention. If a ventricular arrhythmia is detected 602 using ECG based detection 601, a check 604 is made to determine the state of the skeletal muscle signal. If the current state of the skeletal muscle signal is not known or available, the skeletal muscle signal is acquired 606, which may involve activating (i.e., powering-up) a skeletal muscle sensor or detection circuitry.

If a comparison 607 of the skeletal muscle signal to a threshold indicates patient inactivity, the defibrillation capacitor is charged 608 and a shock is delivered 610 to treat the arrhythmia. If, however, comparison 607 of the skeletal muscle signal to the threshold indicates patient activity or consciousness, a delay period is initiated and a recheck 614 of the electrocardiogram signal is made after expiration of the delay period. If the electrocardiogram signal indicates or confirms the continued presence of a ventricular arrhythmia after having previously checked the skeletal muscle signal at block 606, the defibrillation capacitor is charged 608 and a shock is delivered 610.

In this illustrative approach, re-evaluation of the detected ventricular arrhythmia using the skeletal muscle signal is performed once, so that treatment of a confirmed ventricular arrhythmia is not unduly delayed. It is noted that a ventricular arrhythmia re-verification routine may be performed during capacitor charging prior to shock delivery.

An ITCS device may operate in a batch mode or adaptively, allowing for online or off-line implementation. To save power, the system may include the option for a hierarchical decision-making routine that uses algorithms known in the art for identifying presence of arrhythmias or noise in the collected signal and judiciously turning on and off the skeletal muscle signal detection routine of the present invention.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An implantable cardiac stimulation device, comprising:
   a housing configured for subcutaneous non-intrathoracic placement in a patient;
   energy delivery circuitry provided in the housing;
   detection circuitry provided in the housing;
   one or more electrodes coupled to the energy delivery and detection circuitry and configured for subcutaneous non-intrathoracic placement in a patient, the one or more electrodes sensitive to cardiac and muscle activity; and
   a processor provided in the housing and coupled to the energy delivery and detection circuitry, the processor for detecting a arrhythmia using a cardiac signal developed from the sensed cardiac activity and detecting an activity state of the patient using an activity signal developed from the sensed muscle activity, the processor for modifying delivery of a therapy that treats the arrhythmia in response to the activity signal.

2. The device of claim 1, wherein the processor inhibits delivery of the arrhythmia therapy in response to the activity signal exceeding an activity threshold.

3. The device of claim 1, wherein the processor inhibits delivery of the arrhythmia therapy in response to the activity signal indicating patient consciousness or movement.

4. The device of claim 1, wherein the processor inhibits delivery of the arrhythmia therapy for a predetermined time period in response to the activity signal exceeding an activity threshold, and withholds delivery of the arrhythmia therapy upon expiration of the predetermined time period and cessation of the arrhythmia.

5. The device of claim 1, wherein the processor inhibits delivery of the arrhythmia therapy for a predetermined time period in response to the activity signal exceeding an activity threshold, and delivers the arrhythmia therapy upon expiration of the predetermined time period and non-cessation of the arrhythmia.

6. The device of claim 1, wherein the processor inhibits delivery of the arrhythmia therapy in response to the activity signal exceeding an activity threshold, and wherein the processor provides a notification that the arrhythmia therapy is inhibited.

7. The device of claim 1, wherein:
   in response to the activity signal indicating patient consciousness or movement, the processor inhibits delivery of the arrhythmia therapy; and
   in response to detection of a life-threatening arrhythmia, the processor immediately delivers the arrhythmia therapy irrespective of the activity signal.

8. The device of claim 1, wherein the processor receives an electrocardiogram using the detection circuitry and discriminates the cardiac signal and the activity signal from the electrocardiogram.

9. The device of claim 8, wherein the processor discriminates the cardiac and activity signals using a signal separation technique.

10. The device of claim 8, wherein the processor discriminates the cardiac and activity signals using blind source separation.

11. The device of claim 8, wherein the one or more electrodes comprises:
    a first combination of electrodes adapted to preferentially sense cardiac signals associated with the cardiac activity; and
    a second combination of electrodes adapted to preferentially sense noise signals associated with the muscle activity.

12. The device of claim 11, wherein:
    the one or more electrodes comprises a plurality of electrodes;
    the processor selects combinations of the plurality of electrodes; and
    the processor senses a cardiac signal component and a noise component of signals acquired by each of the controller selected electrode combinations.

13. The device of claim 1, wherein the processor detects the arrhythmia using morphology based arrhythmia detection.

14. The device of claim 1, wherein the processor detects the arrhythmia using rate based arrhythmia detection.

15. The device of claim 1, wherein the one or more electrodes comprise a plurality of electrodes, and wherein the processor detects the arrhythmia using an activation sequence over the plurality of electrodes.

16. The device of claim 1, wherein the processor detects the arrhythmia using a cardiac signal curvature.

17. A cardiac stimulation method, comprising:
    detecting signals at one or more subcutaneous non-intrathoracic locations;
    discerning a cardiac signal from the detected signals;
    discerning an activity signal associated with muscle activity from the detected signals;
    detecting a arrhythmia using the cardiac signal;
    detecting a patient activity state using the activity signal; and
    modifying delivery of a subcutaneous non-intrathoracic therapy that treats the arrhythmia in response to the activity signal.

18. The method of claim 17, wherein delivery of the arrhythmia therapy is inhibited in response to the activity signal exceeding an activity threshold.

19. The method of claim 17, wherein delivery of the arrhythmia therapy is inhibited in response to the activity signal indicating patient consciousness or movement.

20. The method of claim 17, wherein delivery of the arrhythmia therapy is inhibited for a predetermined time period in response to the activity signal exceeding an activity threshold, and delivery of the arrhythmia therapy is withheld upon expiration of the predetermined time period and cessation of the arrhythmia.

21. The method of claim 17, wherein delivery of the arrhythmia therapy is inhibited for a predetermined time period in response to the activity signal exceeding an activity threshold, and the arrhythmia therapy is delivered upon expiration of the predetermined time period and non-cessation of the arrhythmia.

22. The method of claim 17, wherein:
in response to the activity signal indicating patient consciousness or movement, inhibiting delivery of the arrhythmia therapy; and
in response to detection of a life-threatening arrhythmia, immediately delivering the arrhythmia therapy irrespective of the activity signal.

23. The device of claim 17, wherein discerning the cardiac and activity signals comprises discriminating the cardiac and activity signals using a signal separation technique on the detected signals.

24. The method of claim 17, wherein discerning the cardiac and activity signals comprises performing a blind source separation on the detected signals.

25. The method of claim 17, wherein detecting the signals comprises detecting the signals using a plurality of electrodes provided at a plurality of non-intrathoracic locations, the electrodes selectively combinable to define a plurality of sensing vectors, and discerning the cardiac and activity signals comprises:
selecting a first sensing vector of the plurality of sensing vectors which is preferentially sensitive to signals associated with cardiac activity; and
selecting a second sensing vector of the plurality of sensing vectors which is preferentially sensitive to signals associated with the muscle activity.

26. The method of claim 17, wherein the muscle activity is indicative of patient movement, and discerning the activity signal comprises detecting an accelerometer signal indicative of the patient movement.

27. The method of claim 17, wherein the arrhythmia is detected using morphology based arrhythmia detection.

28. The method of claim 17, wherein the arrhythmia is detected using rate based arrhythmia detection.

29. The method of claim 17, wherein the arrhythmia is detected using an activation sequence detected by a plurality of electrodes.

30. The method of claim 17, wherein the arrhythmia is detected using a curvature of the cardiac signal.

31. A cardiac stimulation device, comprising:
means for detecting signals at one or more subcutaneous non-intrathoracic locations;
means for discerning a cardiac signal and a muscle activity signal from the detected signals;
means for detecting a arrhythmia using the cardiac signal;
means for detecting a patient activity state using the muscle activity signal; and
means for modifying delivery of a subcutaneous non-intrathoracic therapy that treats the arrhythmia in response to the activity signal.

32. The device of claim 31, wherein the delivery modifying means comprises means for inhibiting arrhythmia therapy delivery in response to the activity signal.

33. The device of claim 32, wherein the delivery modifying means comprises means for immediately delivering the arrhythmia therapy in response to detecting a life-threatening arrhythmia irrespective of the activity signal.

34. The device of claim 31, wherein the discerning means comprises means for separating the cardiac and activity signals respectively from the detected signals.

35. The device of claim 31, wherein the discerning means comprises means for acquiring an accelerometer signal indicative of patient movement.

* * * * *